US00PP33057P2

(12) United States Plant Patent
Hansen

(10) Patent No.: US PP33,057 P2
(45) Date of Patent: May 11, 2021

(54) ***ATHYRIUM* PLANT NAMED 'CRESTED SURF'**

(50) Latin Name: *Athyrium niponicum*
Varietal Denomination: Crested Surf

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 87 days.

(21) Appl. No.: 16/602,729

(22) Filed: Nov. 26, 2019

(51) Int. Cl.
*A01H 5/00* (2018.01)
*A01H 9/00* (2006.01)

(52) U.S. Cl.
USPC ..... Plt./379
CPC ..... *A01H 9/00* (2013.01)

(58) Field of Classification Search
USPC ..... Plt./379
CPC ..... A01H 9/00; A01H 5/00
See application file for complete search history.

*Primary Examiner* — Keith O. Robinson

(57) ABSTRACT

A new and unique crested Japanese fern *Athyrium* plant named 'Crested Surf' characterized by stiff upright habit and compound foliage with alternate deep-green bipinnately with light-green color near the center and wine-colored petioles and midribs. Pinnae and pinnules have compound crested apices.

3 Drawing Sheets

Botanical classification: *Athyrium niponicum.*
Variety denomination: 'Crested Surf'.

STATEMENT REGARDING PRIOR DISCLOSURES UNDER 37 CFR 1.77(B)(6)

The first disclosure of the claimed plant, in the form of a sale, was made by Walters Gardens, Inc. on Jul. 8, 2019. Plants for this sale were obtained from the inventor. Prior to this sale, on Dec. 1, 2018, the plant was first advertised on a website managed by Walters Gardens, Inc. The plant was also listed in the "Walters Gardens 19-20 Catalog' published and released on May 29, 2019. Walters Gardens, Inc. obtained the new plant and all information about the new plant directly from the inventor. No plants of *Athyrium* 'Crested Surf' have been sold, in this country or anywhere in the world, nor has any disclosure of the new plant been made, more than one year prior the filing date of this application, and such sale or disclosure within one year was either derived directly or indirectly from the inventor.

BACKGROUND OF THE INVENTION

The present invention relates to the new and distinct *Athyrium niponicum* given the cultivar name 'Crested Surf' and developed by the inventor in a greenhouse at a wholesale perennial nursery in Zeeland, Mich., USA. Through trials at the same nursery the plant was referred to by the code 09-124-01. The new plant has been successfully asexually propagated initially by division in 2015 followed by shoot tip tissue culture at the same nursery in Zeeland, Mich. Both these asexual propagation systems has been found to produce stable and identical plants that maintain all the unique characteristics of the original plant in successive generations.

BRIEF SUMMARY OF THE INVENTION

*Athyrium* 'Crested Surf' differs from its parents as well as all other *Athyrium* known to the applicant. The present invention has not been evaluated under all possible environmental conditions. The phenotype may vary with changes to the growing conditions such as light intensity or duration, nutrient availability, water availability, etc. without any change to the genotype. The most similar known *Athyrium* cultivars known to the inventor are: *Athyrium* hybrid 'Ocean's Fury' U.S. Plant Pat. No. 20,126, *Athyrium filix-femina* 'Dre's Dagger' (not patented), *Athyrium niponicum* 'Joy Ride' (not patented), *Athyrium niponicum* 'Thrill Seeker' (not patented) and *Athyrium niponicum* 'Apple Court' (not patented). 'Ocean's Fury' has a taller and narrower habit, less creating branching, smaller pinnules and with less reddish stems. 'Dre's Dagger' has finer textured foliage, narrower leaf blades, paler green leaf color without the wine-colored petiole and pinna and pinnule midribs, and without the light green variegation near the middle of the pinna and pinnules. 'Joy Ride' has more compact habit, more tasseled with less red on the stems. 'Thrill Seeker' has more cresting with less red in the stems and less upright habit. 'Apple Court' has less vigor and less upright with pinnae that are broader. The female and male parent was shorter than 'Crested Surf'.

The new plant, 'Crested Surf', is unique from all ferns known to the inventor by the following combined traits:

1. Stiff upright habit;
2. Foliage serrate, finely-textured, broadly-lanceolate, bipinnately compound with alternating deep green and light green portions of the pinnae and pinnules;
3. Pinnae and pinnules with compound crested apices;
4. Petioles and midribs with wine coloration.

BRIEF DESCRIPTION OF THE DRAWINGS

The color drawings illustrate the overall characteristics of the new plant and demonstrate the overall appearance of the new plant including the unique traits as a three-year-old plant growing in a shaded trial garden in Zeeland, Mich. with supplemental water and fertilizer as needed. The colors are as true as reasonably possible given the technology available. The colors are as accurate as reasonably possible with color reproductions. Ambient light, spectrum, temperature, source, duration and direction may cause minor variation in appearance.

DETAILED DESCRIPTION OF THE INVENTION

Figure 1:
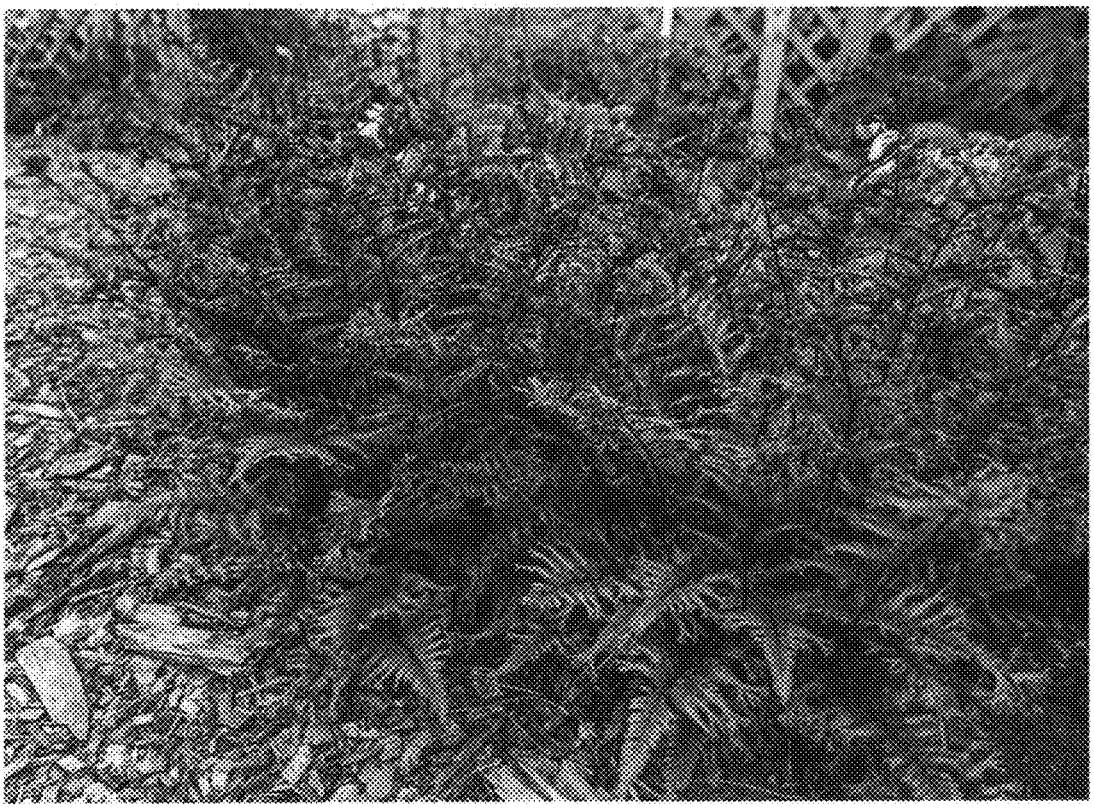
FIG. 1 shows the new plant grown in a shaded trial garden.
Figure 2:
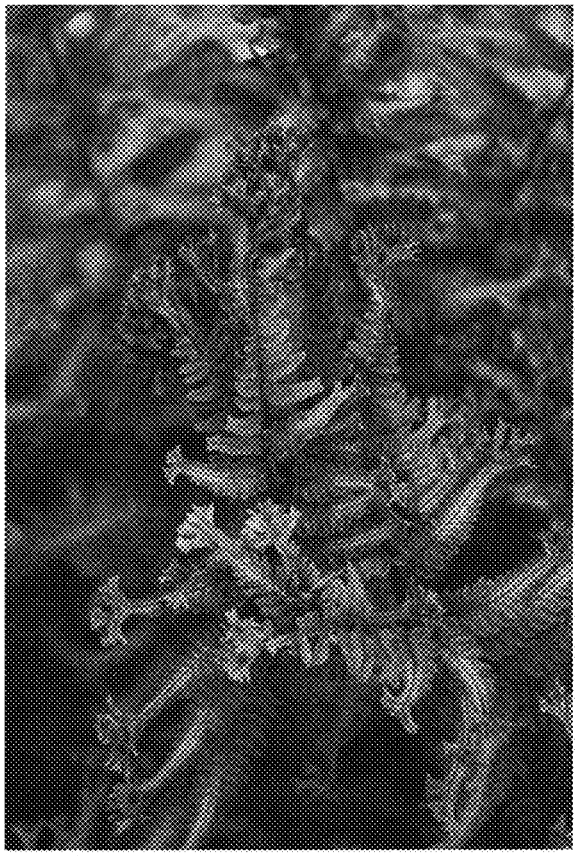
FIG. 2 shows a close-up of the top of the foliage and apical cresting.
Figure 3:
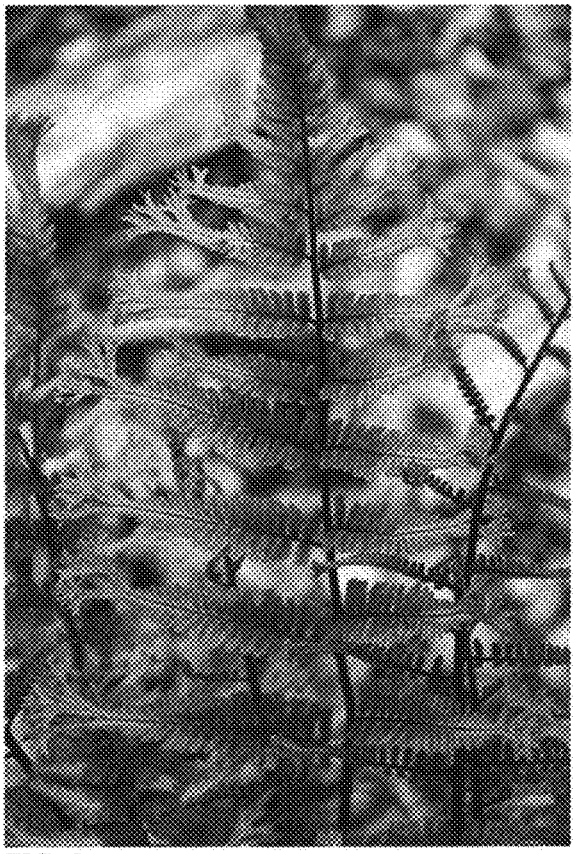
FIG. 3 shows a close-up of the top of the foliage and marginal cresting.
Figure 4:
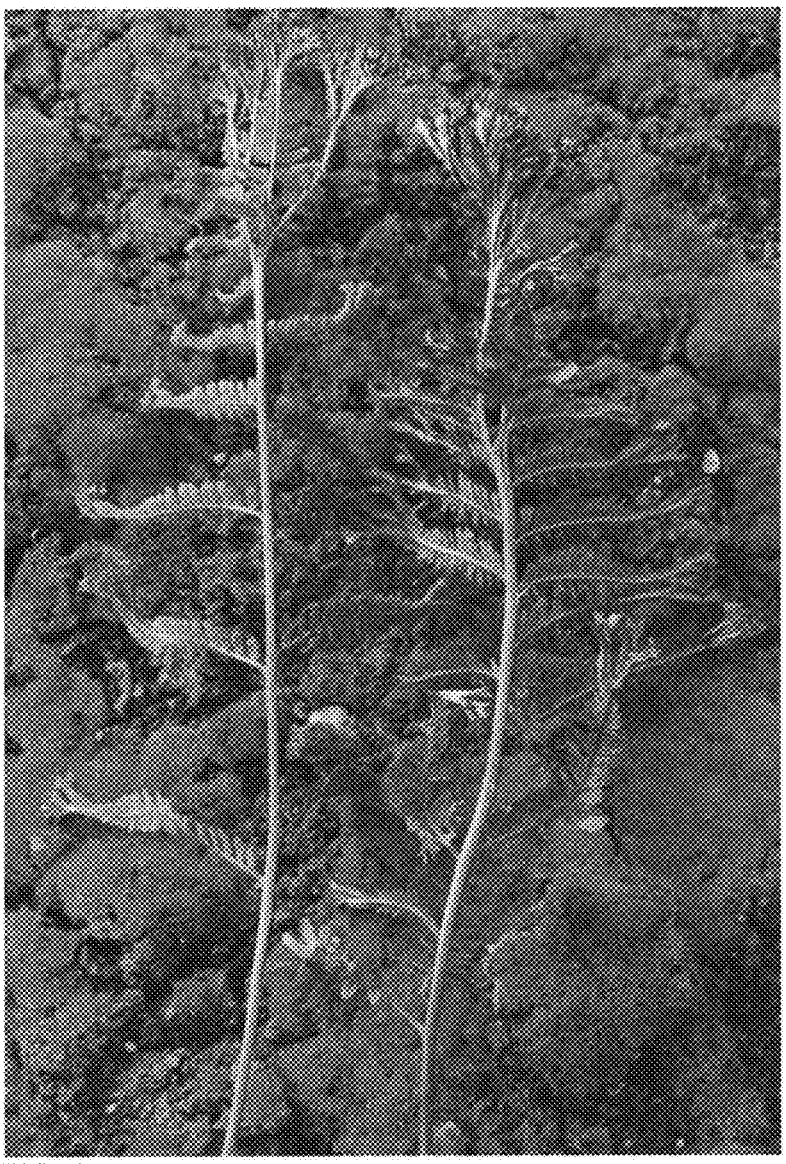
FIG. 4 shows a close-up of the back of the foliage of the new plant with sporangium and cresting.

The following detailed description is based on a three-year-old plant growing in a shaded trial garden in Zeeland, Mich., USA. Environmental conditions for the growing season daytime temperatures range between 12-30° C., and night temperatures range between 6-19° C. Except for ordinary dictionary color usage, color references are according to The Royal Horticultural Society Colour Chart, 2015 edition.

Parentage: Female or egg parent is an unnamed proprietary selection of *Athyrium niponicum* (not patented); male or sperm parent is the same unnamed proprietary selection of *Athyrium niponicum* (not patented);

Asexual propagation: Plant tissue culture, time to finish as from a 25 mm plug to a 3.8 liter container about 10 to 12 weeks;

Plant habit: Herbaceous clumping mound; winter-hardy; to about 112.0 cm wide and 60.0 cm tall;

Root: Fibrous; heavily branching; color variable, active tips translucent nearest RHS 4D with area behind tip nearest RHS NN155C and older roots nearest RHS 165C;

Foliage: Broadly-lanceolate; bipinnately compound; pinnae lanceolate with broadly crested apices, cresting compound with up to four main branches; pinnatisect; pinna also compound crested with typically two main branches; pinnule margin serrate, apices acute distally to proximally crested or emarginate; surface glabrous and matte both adaxial and abaxial;

Foliage size: Blade size to 27.0 cm long and 15.0 cm wide and apical crests to 60.0 mm wide; pinna size to 10.0 cm long and 30.0 mm wide at base with apical crests to 24.0 mm wide; pinnule size to 17.0 mm long and 3.0 mm wide;

Foliage color: Young expanding adaxial toward base and apex of pinna nearest RHS NN137A with portion nearest RHS 148D, abaxial nearest blend between RHS NN137D and RHS 138A; mature adaxial toward base of pinna and margin of pinnule nearest RHS NN137B with center of pinnule having undertone of nearest RHS N187A and center of pinna and pinnule nearest RHS 193A, abaxial nearest RHS 137A;

Petiole: Stiff; cylindrical; mostly upwardly to slightly outwardly; glabrous with chaffy scales to about 3.0 mm long and 0.3 mm across, scale color nearest RHS 164D;

Petiole size: To 43.0 cm long and 5.0 mm across at base;

Petiole color: On expanding leaves nearest RHS NN137A with undertone of RHS N186C, mature leaves nearest RHS N186C;

Veins: Pinnate;

Vein color: Same as surrounding tissue with adaxial and abaxial midribs nearest RHS N186C proximally and in abaxial distal one-quarter transitioning to nearest RHS 155A and adaxial distal one-quarter transitioning to nearest a blend between RHS 182D and RHS 155A;

Fruiting body: Sporangia in sori on pinnules; sori clusters to 2.0 mm long and 1.0 mm wide; color immature nearest RHS 197D, mature sporulating nearest RHS 166D; indusium on side closest to rachis; fertility has not been tested;

Diseases and pests: Although some *Athyrium* develop rust, none has been observed on the new plant. No other specific pests or diseases or immunities have been observed on 'Crested Surf'. The new plant is winter hardy from USDA zones 3 through 8.

I claim:

1. A new and distinct cultivar of ornamental fern *Athyrium* plant named 'Crested Surf' as herein described and illustrated.

* * * * *